United States Patent [19]

Chvapil et al.

[11] Patent Number: 4,913,897
[45] Date of Patent: Apr. 3, 1990

[54] USE OF HYDROGEL SOLUTIONS TO FORM A HYDROPHILIC PROTECTIVE FILM ON THE SKIN AGAINST TOXIC SUBSTANCES, POLLUTANTS, INFECTIONS AND SKIN SECRETIONS

[75] Inventors: Milos Chvapil; Stuart A. Hoenig, both of Tucson, Ariz.

[73] Assignee: Bio-Products, Inc., Tucson, Ariz.

[21] Appl. No.: 139,300

[22] Filed: Dec. 28, 1987

[51] Int. Cl.⁴ .................................. A61K 7/42
[52] U.S. Cl. ........................ 424/59; 424/61; 424/69; 424/422; 424/405; 514/944; 252/315.01; 252/315.1; 427/1
[58] Field of Search ............ 424/69, 422, 405, 59, 424/61; 514/944; 252/315.01, 315.1; 427/1

[56] References Cited

U.S. PATENT DOCUMENTS

| | | | |
|---|---|---|---|
| 3,708,435 | 1/1973 | Starkman | 424/69 |
| 3,880,158 | 4/1975 | Gurney | 521/148 |
| 3,975,350 | 8/1976 | Hudgin et al. | 524/233 |
| 4,156,066 | 5/1979 | Gould | 424/422 |
| 4,156,067 | 5/1979 | Gould | 424/422 |
| 4,255,550 | 3/1981 | Gould | 528/84 |
| 4,331,783 | 5/1982 | Stoy | 525/294 |
| 4,337,327 | 6/1982 | Stoy | 525/294 |
| 4,370,451 | 1/1983 | Stoy | 525/328.4 |
| 4,379,874 | 4/1983 | Stoy | 525/294 |
| 4,420,589 | 12/1983 | Stoy | 525/294 |
| 4,424,305 | 9/1982 | Gould et al. | 525/455 |

Primary Examiner—Ellis P. Robinson
Assistant Examiner—P. J. Ryan
Attorney, Agent, or Firm—Cahill, Sutton & Thomas

[57] ABSTRACT

A thin film of hydrophilic hydrogel is applied to a person's skin, including hands, forearms, and face to prevent shedding of minute skin particulates, to prevent fingerprints, and to prevent transmission of toxic substances through the film.

10 Claims, 1 Drawing Sheet

USE OF HYDROGEL SOLUTIONS TO FORM A HYDROPHILIC PROTECTIVE FILM ON THE SKIN AGAINST TOXIC SUBSTANCES, POLLUTANTS, INFECTIONS AND SKIN SECRETIONS

BACKGROUND OF THE INVENTION

The outer skin layer (epidermis) contains both hydrophilic and hydrophobic substances, represented mostly by proteins-polysacharrides and lipids, which allow for slow but definite penetration of both water and lipid-soluble small molecule substances across the stratum corneum layer into the skin tissue. It is well established that the stratum corneum, forming the upper layer of the epidermis, is the structure controlling the absorption of various substances into the skin and tissues.

There are situations when the body or skin areas exposed to the environment can be contaminated with industrial or military toxic substances, which are soluble in lipids and lipid solvents. These substances will not penetrate across a hydrophilic layer if such a layer forms a continuity over the skin surface. A typical example of a high risk industrial toxic substance is parathion, which is used commonly as an agricultural insecticide. It is practically insoluble in water, thus it will not penetrate the hydrophilic layer of a hydrogel with high water content, but will be resorbed by unprotected skin. This can cause severe health risks to the exposed person. The same principle is applicable to several lipid-soluble toxic substances used as chemical weapons, e.g., vesicant mustard gas, or neurotoxic substance VX, which are oily substances that do not penetrate the temporary second skin formed by hydrophilic film.

The stratum corneum layer is also a barrier to disease organisms. It is known that infectious agents, such as viruses or bacteria, can inflict general infection and disease only if the skin integrity is impaired by cuts, rashes, or abrasions. This is especially important with human immunodeficiency viral (HIV) infections, which could be transmitted through skin-penetrating wounds inflicted by instruments, needles or from a manicure around the nail bed. Another possible entry for HIV, causing lethal AIDS, may be the exposure of broken skin to HIV through skin abrasion in the perianal region or as acute dermatitis (rash) when exposed to vaginal secretions during intercourse.

A major source of contamination is certainly through contact with the blood of AIDS patients. For this reason, rubber gloves were introduced in the state of New Jersey for the police force when dealing with potentially wounded criminals, in boxing, etc. This reflects the fear of the public of becoming contaminated by HIV. There is no doubt that the medical staff has the highest exposure risk not only to HIV, but to mycobacterium, tuberculosis or hepatitis B virus.

So far situations have been discussed wherein substances of a chemical or biological nature present in the environment could penetrate across the stratum corneum barrier into the body. However, the skin contains the sweat and sebaceous glands. Their distribution and concentration vary at different skin areas. The fingers and palm of the hand have relatively high densities of these glands, which are responsible for insensible perspiration or formation of the greasy sebum, a lipid-rich product that lubricates the surface of the skin and keeps the stratum corneum oiled. The volume of sweat-solution loss in an adult male varies between 0.5 and 4.0 liters per day. There are approximately 6000 sebaceous glands per square inch of the thick skin area. Besides various electrolytes (sodium, potassium, chlorine, etc.), sweat contains many water soluble substances, such as amino acids and vitamins. By sweating, the skin functions as an excretory organ. Both secretion products of sweat and sebaceous glands form an integral layer on the skin surface which leaves visible fingerprints when a smooth surface is touched, such as a mirror. There are professions, such as those which deal with the manufacturing of semiconductors, and work with optical lenses and similar objects, where these greasy marks will interfere with product quality. In these professions the employees use not only hair caps and facial masks, but also impermeable rubber gloves in order to minimize product contamination from fallout of skin scales or from body secretory products, represented mainly by oily products of the sebaceous glands. However, the relatively thick rubber gloves interfere with the fine tactile sensations needed for the work with small objects. Also, the impermeability of the rubber glove results in accumulation of the sweat and heat underneath the glove. Long term wearing of gloves may reduce heat loss to the point that the wearer suffers from thermal shock. There have been some attempts to use skin creams or collagen based lotions or creams to deal with the foregoing problems. These formulations do not form a hydrophilic protective layer, as fat is a common component of these cosmetic formulations. Thus, the protection achieved has been minimal.

Clearly, there is a need for an improved hand and skin protection system that does not involve rubber latex gloves. Gloves have been part of the clean room environment for many years and are known to be effective in reducing particular contamination from human hands. However, the gloves begin to generate particulates after several hours of use. Also, glove materials (e.g., latex nitrile, vinyl, etc.) vary in smoothness, thus affecting the ability of the manufacturer to clean the surface before packaging. Rough surfaces generally shed particulates and can transfer contaminant materials from one process to the other. Vinyl gloves are very smooth and easy to clean, however, they are an 80% dioctylphthalate (DOP) plasticizer. If a wearer of vinyl gloves presses a finger on a clean, smooth surface, fingerprinting will be observed because of the DOP being pressed out of the polymer.

Even the thinnest gloves reduce tactile sensitivity and the feedback that is needed to control delicate movement. Perspiration accumulates under the gloves, particularly with the no-powder gloves used in clean rooms.

In any case, glove technology cannot be used to reduce the shedding of skin flakes from the employee's face. If a mask is worn it may abrade the skin and increase particle generation. The response of employees to both masks and gloves is generally negative. One advantage of gloves is that it is difficult not to wear them properly. With masks, however, the situation is much different; it is difficult to get the employees to wear them properly.

It has been found that a major source of particles in the range from 0.2 microns to 5 microns in the ambient air is produced by flexing of human skin, especially skin between joints, such as finger joints, and from the eyelids. Minute particles of skin continuously flake off during normal movement of such skin. Consequently, obtaining extremely clean, particulate-free environment for manufacturing areas in clean rooms required for manufacture of high yield integrated circuits and the like requires provision of a means for preventing flaking of such skin particles from workers.

All of these problems suggest the need for a skin coating material that would stop contamination from oils and skin flakes while at the same time not being greasy or irritating to the skin. Naturally, the material must be easy to remove when the employee goes out on break, to lunch or home for the day.

OBJECTS OF THE INVENTION

It is an object of the invention to provide a method of forming a thin layer over the skin, which layer can be referred to as a "second skin", by application of soluble hydrogels, which after evaporation of the solvent forms a solid, continuous, hydrophilic, pliable, flexible, elastic, mechanically strong cover.

Another object of the invention is to provide a thin film covering the skin, mainly the fingers, without loss of tactile sensation, and allowing the evaporation of perspiration fluid.

Another object of the invention is to provide a technique for preventing shedding or flaking of human skin particulates in the size range of 0.2 microns to 5 microns due to normal movement of human skin.

Another object of the invention is to prevent penetration of toxic substances into the body across the skin.

Another object of the invention is to prevent viral infections through cuts in the skin.

Another object of the invention is to form a "second skin" not only as a mechanical barrier but also as a chemical infection barrier to antidotes, bactericidal or virucidal substances or insect repellents.

Another object of the invention is to eliminate oily fingerprints on smooth surfaces.

Another object of the invention is to form a thin layer over fingers and face, which film is easy to remove.

Another object of the invention is to provide a technique for visibly detecting whether or not a worker is wearing a layer of the type described.

BRIEF DESCRIPTION OF THE INVENTION

Briefly described, and in accordance with one embodiment, and in order to prevent the penetration of toxic substances or infections through the skin or to eliminate the contamination of external objects by skin secretions (sebum, sweat) or skin flakes, I have developed a method of covering the skin, mainly on the exposed areas of fingers, hands, arms and face, with a continuous, thin layer of a mechanically strong hydrophilic hydrogel. The optimal polymers to cover the skin with a thin layer of a film are soluble in nontoxic, skin-nonirritating solvents such as ethyl alcohol and isopropyl alcohol. The polymers are hydrophilic, preventing the passage of lipophilic substances in either direction across the film formed over the skin surface, so there is no transport of sebum-sweat components from the skin or hydrophobic toxic substances or infectious materials from the environment across the polymer film. The polymeric solution forms a thin film, which has the following characteristics: (a) it forms a continuous layer on the skin surface without breaks or ruptures (b) it is pliable (soft), (c) it has mechanical strength mimicking the elasticity of rubber (latex) gloves, (d) it is permeable to water, thus preventing the accumulation of sweat underneath the polymer film and allowing for heat loss.

The hydrophilic nature of the polymer film is enhanced by controlled swelling of the film due to perspiration, the control of the swelling being accomplished by selection of film material. Generally, the magnitude of the swelling should be minimal in order to minimize the adverse effects of swollen film on the loss of mechanical characteristics of the film. Among the mechanical properties, the elasticity, tensile strength and resistance to abrasion are of great importance to the functionality and durability of the thin hydrogel film. The polymeric solutions also are mixable with antidotes against external toxic substances, with antibacterial and antiviral agents, and with insect repellents to form a film that forms not only a mechanical but also a chemical barrier. Finally, the polymeric film adheres firmly to the skin surface, but is removable without using drastic, skin injury infecting procedures. A coloring agent can be used to make it readily apparent whether a worker is wearing the thin hydrogel layer.

Polymers suitable for use as a skin protective film include hydrophilic polyurethanes soluble in alcohols, dimethylsulfoxide or other physiologically acceptable organic solvents. These hydrophilic polyurethanes exist in a variety of solutions in the above-mentioned solvents, differing only in the molecular weight of the polymeric chain. Once the solvent evaporates, the formed film has controllable affinity for fluids. It also has good physical properties, i.e., the film remains flexible and has a controlled moisture vapor transmission, allowing the evaporation of the perspiration fluid and loss of body heat. These hydrogels based on polyurethanes are a family of hydrophilic polymers which in the presence of hydrogen bonding fluids are converted to hydrogels, each taking up fluids to a predetermined equilibrium level. These soluble polymers form a homogenous gel, cream, or viscous liquid or can be prepared in a form suitable for dispensing from a spray can and can be spread onto the skin surface to evaporate into a solid thin film of polymer coating. These polyurethanes can be available in forms with controllable ethanol/water content and with broad range of mechanical properties. The hydrophilic polyurethanes we found to be suitable are disclosed in U.S. Pat. Nos. 3,975,350, 4,156,066, 4,156,067, 4,255,550, and 4,424,305, all incorporated herein by reference.

In the examples herein, several hydrophilic polyurethane hydrogels referred to as "polyurethane D-3" and "polyurethane D-4" are described as follows:

| polyurethane D-3: | glycol molecular weight | = 600 daltons |
|---|---|---|
| | percent isocyanate | = 25% |
| | percent glycol | = 75% |
| polyurethane D-4: | glycol molecular weight | = 400 daltons |
| | percent isocyanate | = 30–40% |
| | percent glycol | = 60–70% |

Particularly advantageous was a polymeric hydrogel based on polyurethane D-4, containing chains of glycols around 450 daltons, leaving approximately 61 weight percent of glycols and approximately 39 weight percent of isocyanate, which was tested for tissue reactivity and found most biocompatible while forming a mechanically strong film, as shown by Example 1.

Other polymeric compositions that are suitable for the present invention are disclosed in U.S. patent application "Injectable Physiologically Acceptable Polymeric Compositions", Ser. No. 646,243, filed Aug. 31, 1984, incorporated herein by reference. Included among suitable polymeric compositions are hydrophilic hydrogels, including polymers and copolymers of acrylonitrile and polyvinylactate, also linear or slightly branched polymers and copolymers of 2-hydroxethylacrylate and methacrylate, hydrophilic polyurethanes D-3, D-4, etc., in suitable solvents. Also included are polymers and copolymers of acrylonitrile, particularly copolymers with other derivatives of acrylic acid, such as acrylamide, N-substituted acrylamide, acrylhydrazide N-substituted acrylhydrazide, glutarimide, vinylsufonate acid, acrylic acid and its salts; polyvinylacetate, its copolymers and particularly poly (vinylacetate-covinylalcohol); linear or slightly branched polymers and copolymers of 2-hydroxyethyl acrylate and methylacrylate; poly (N vinylliminocarbonyl); and polycondensates and polyadducts, such as poly(oxyethyleneoxy carbonylimino-1,3 -phenyleniminocarbonyl); poly(oxy-1,4-phenylensulfonyl-1,4-phenylene); poly(imino(1-oxoundecamethylene); poly(pyromellitio dianhydride-co-aromatic amines), or polymaic acid. Preferably such polymeric compounds are those which are soluble in dimethylsulfoxide DMSO but insoluble in water, as more fully hereinafter discussed. Particularly advantageous polymeric compounds are those containing at least 2% nitrile groups, such as the polyacrylonitrile and copolymers of acrylonitrile with various, particularly hydrophilic comonomers. A particularly advantageous acrylonitrile copolymer is produced by the partial acid-catalyzed hydrolysis of a polymer containing at least 85 molar percent acrylonitrile units. Polyacrylonitrile and its copolymers, if coagulated from solution of sufficiently high viscosity, forms pseudo-hydrogels (or "aquagels"). The aquagel contains up to about 75% of water, more usually 30 to 60% of water. The water acts as a plasticizer, even if the polymer itself is non-swellable, for essentially an unlimited time period. Such an aquagel thus formed in tissue is a semirigid material suitable, for example, for facial bone augmentation. Hydrogels suitable for the invention are copolymers containing both hydrophilic and hydrophobic groups, such as vinylacetate-vinylalcohol or acrylonitrile-acrylmide. More particularly suitable are copolymers in which both hydrophobic and hydrophilic groups are organized in continuous sequences, or block copolymers, such as described in U.S. Pat. Nos. 4,379,874, 4,420,589, 4,331,783, 4,337,327 and 4,370,451 (incorporated herein by references) and which are particularly suited for the present invention.

The solvent or solvent system of the present invention for the above polymeric compounds should be polar, miscible with water, and nontoxic. Preferred solvents for the present invention are the nontoxic water miscible solvents having a molecular weight below about 200, exhibiting moderate to strong hydrogen bonding capability and having a preferred solubility parameter between 10 and 15 $(cal/cc)^{\frac{1}{2}}$ for moderate H-bonding and between 11 and 20, e.g., between 12.5 to 17) for stronger H-bonding. Examples of such solvents are dimethylsulfoxide (DMSO), glycerol, glycerol monoacetate, glycerol diacetate (diacetin), methanol, ethanol, propanol, isopropanol, cyclic ethylene carbonate, cyclic propylene carbonate, dimethyl formamide, tetramethylene sulfoxide, N-N-diethylacetamide, N-N-dymethylacetamide, ethylene glycol, proplene glycol, triethylene glycol and diethylene glycol and mixtures thereof.

In principle, these polymers are insoluble in water or tissue fluids below a temperature of about 50° C., are free of any toxic component which would be released into tissue, are soluble in polar, water miscible, nontoxic solvents, and finally, they solidify after evaporation of the solvent. A solid hydrogel polymer absorbs some water, which increases its hydrophilic nature and pliability.

These hydrogel films, 10 to 350 microns thick, are soft, pliable, and resist cracking or rupturing under slight stretching caused by finger and hand movements. They also resist abrasion on repetitive touching of instruments. Finally, if exposed to aqueous media (e.g., sweat) they retain some (but minimal) water. In general, an appropriate hydrogel solution is uniformly spread over the exposed skin areas and left to dry for a few minutes. Various alcohols that are nontoxic and nonirritating to the skin, e.g., ethyl alcohol, n-propyl and isopropyl alcohol, can be used as solvents of these hydrogel polymers. Other suitable solvents include dimethylsulfoxide (DMSO) and glycerol. The volatile nature of alcohols or DMSO ensures fast evaporation of the solvent. Once the hydrogel dries, it is water insoluble. The insensible (permanent, continuous) perspiration hydrates the thin layer, thus increasing its hydrophility, making it more pliable.

DESCRIPTION OF THE PREFERRED EMBODIMENTS

Figure 1A:
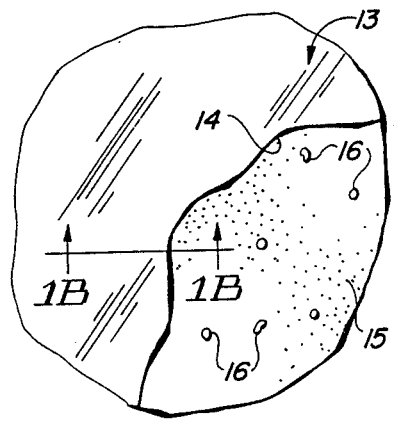
FIG. 1A is an enlarged plan view of detail 1A of FIG. 1.
Figure 1:
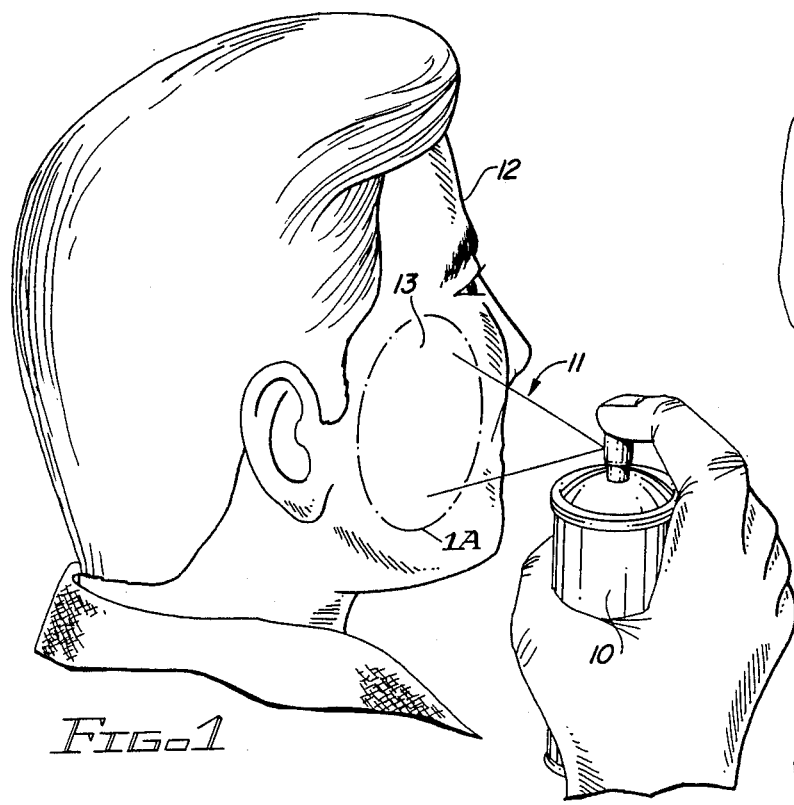
FIG. 1 is a diagram illustrating application of a hydrophilic hydrogel film onto the face of a user to prevent shedding of skin flakes from the person's skin.

Referring now to FIG. 1, an aerosol spray 11 is applied from an aerosol can 10 to form a thin hydrophilic hydrogel layer on a face 12 of a worker. In accordance with the present invention, the hydrophilic hydrogel layer can be composed of various polymers mixed in various solvents, to form a thin, transparent, pliable but tough protective layer 10 to 200 microns thick which prevents the worker's face from shedding minute skin particles into the atmosphere in an industrial or medical "clean room" environment and/or to protect the user from absorbing airborne contaminants which might otherwise come in contact with the worker's skin. The layer also allows the nerve ends in the user's skin to accurately sense surfaces with which the skin comes in contact. FIG. 1A, which shows an enlarged view of an araa 13 of the user's face after the hydrogel film has dried, shows a cutaway portion in which the bare skin 15 is exposed. Reference numeral 16 designates various minute skin flakes that are continually being generated and shed by a person's skin, especially at the location of joints and at the eyelids. Such skin flakes are typically approximately 0.2 to 5 microns in size, and, when airborne, can cause defects in manufacture of semiconductor devices and can contaminate other materials.

Numeral 14 designates the smooth, tough, pliable hydrophilic hydrogel film after drying. Typically, the hydrogel film 14 can be easily removed by peeling it off (and applying heated water if difficulty is encountered) after the work day has ended.

Figure 1B:
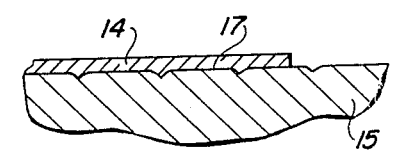
FIG. 1B is a partial cross-section across section line 1B—1B of FIG. 1A.

FIG. 1B shows a section view across section line 1B—1B of FIG. 1A, in which numeral 17 designates the irregular interface between the hydrogel film 14 and the skin substrate 15. The outer surface of film 14 is very smooth compared to the irregular surface 17 in which the skin flakes 16 are trapped.

Figure 2A:
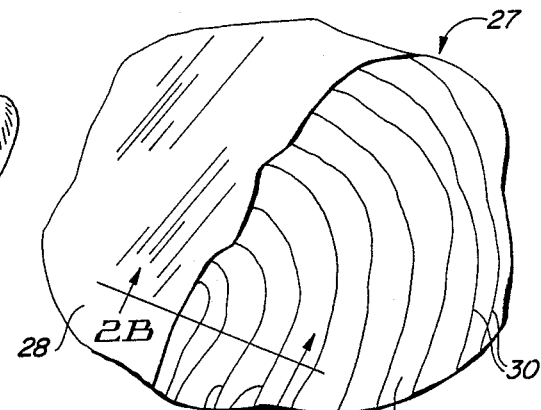
FIG. 2A is an enlarged view of detail 2A of FIG. 2.
Figure 2:
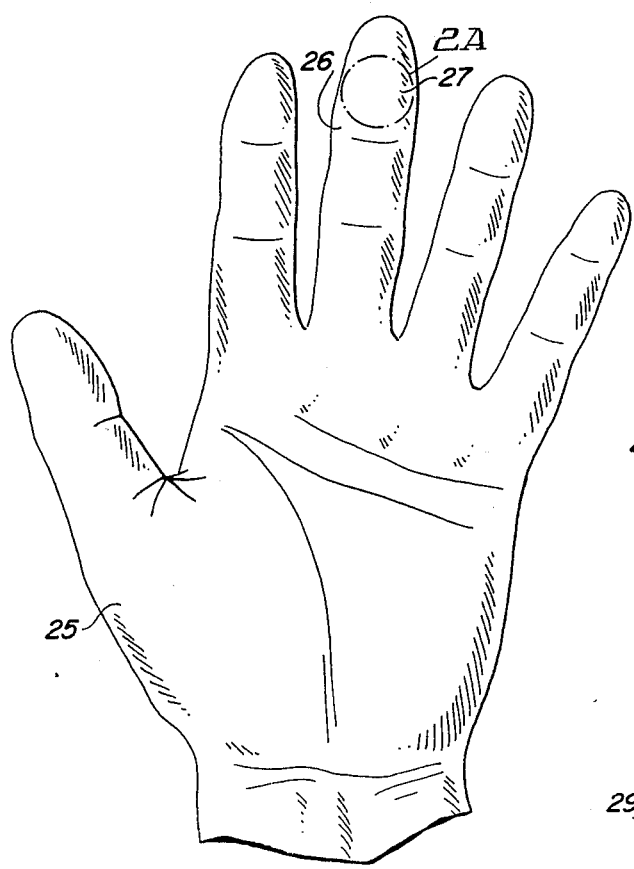
FIG. 2 is a diagram of a worker's hand having a hydrophilic hydrogel film formed thereon.
Figure 2B:
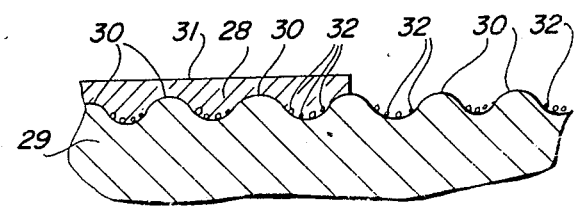
FIG. 2B is a sectional view across section line 2B—2B of FIG. 2A.

In FIG. 2, a worker's hand 25 is covered with a hydrophilic hydrogel layer, by means of an aerosol spray such as 11 in FIG. 1, or by smooth spreading of a hydrogel viscous solution, or a cream uniformly over the user's hands and fingers. An enlarged area 2A of the user's finger 26 is shown in FIG. 2A. Reference numeral 28 designates the hydrogel film, and fingertip skin surface 29 is exposed in a cutaway portion of the film 28. Reference numeral 30 designates ridges that define the user's fingerprint pattern. The sectional view in FIG. 2B shows the irregular ridges 30 between the fingertip skin 29 and the hydrogel layer 28 thereon. The upper surface 31 of the hydrogel layer 28 is very smooth compared to the ridges 30 of the finger skin surface 29. As described in the following examples, the hydrogel layer 31 prevents insensible perspiration or greasy sebum from passing from the finger surface 29 to the upper surface of the hydrophilic layer 28, and thereby prevents the fingertips of the user from leaving fingerprints on items touched.

The following examples serve to illustrate the practice of the invention but are not to be regarded as limiting. All parts are given by weight unless otherwise specified.

EXAMPLE 1

This example describes physical characteristics of hydrogel films made by various types of polyurethanes, differing in the average length of the glycol unit of the polymer and volume of glycols and isocyanate.

As a starting solution of polymers, polyurethane D-4 and D-3 were used. The average molecular size of the D-4 glycol chain was 450 daltons, and D-3 was 20–30% longer chains. D-4 was prepared as 15 weight percent in ethanol:water (7:3), and D-3 as 10 weight percent solution also in ethanol:water (7:3). I tested three concentrations of the above solution and in addition with glycerol. Solution 1 consisted of plain D-4 polymer. Solution 2 consisted of D-4 and glycerol mixture (10:1). Solution 3 contained D-4 and D-3 in a ratio of 5:1. Individual solutions were coated on a glass in the volume of 0.2 cubic centimeters 6.25 square centimeters to form 100 micron thick film (film 1, film 2, and film 3 in Table 1) when dry. These films were further tested for water absorption (swelling) and tensile strength using Instron Mechanical Strength Tester, Model 1001. The same solutions were coated on the skin surface of dead nude mice, with the same volume of 0.2 microliters spread over a 6.25 square centimeter area. At various times the (1) adhesiveness of the drying polymer to the skin surface and (2) the stickiness of one polymer film to another film were tested. Both criteria were evaluated semi-quantitatively on a scale from 1 to 5:

1 represents no adhesion or stickiness.

2 represents minimal adhesion or stickiness; minimal stickiness means that when two fingers with the hydrogel layers thereon are pressed together, and then are separated, there is a barely discernable stickiness, but no visible deformation of the hydrogel surface due to such stickiness as the fingers are separated.

3 represents moderate adhesion or stickiness; when fingers on which a film of the hydrogel has dried are rubbed together so as to produce friction, the film starts separating from the skin; moderate stickiness means that a bit of visible interaction between the hydrogel layer surfaces occurs as the fingers are separated and a number of fiber-like strands stretch and break between the fingers as they are separated.

4 represents good adhesion or substantial stickiness; when fingers on which the film of hydrogel has dried ar frictionally rubbed together, the film does not separate from the skin; substantial stickiness means that irreversible deformation of each hydrogel layer occurs as the fingers are separated, destroying the continuity of the hydrogel layers on each finger.

5 represents very good adhesion or very high stickiness; the hydrogel film doesn't separate from the fingers even when they are very vigorously rubbed together; high stickiness means that particles of each hydrogel layer permanently stick to the other hydrogel layer on the fingers are separated.

Note that very good adhesion with very little stickiness is the most desirable combination of qualities of the hydrogel film.

Table 1 shows the results. The data show that a combination of D-4 with D-3 provides the stronger, very skin adherent and non-sticking film which was considered to have optimal characteristics. The addition of glycerol produces a less adherent, more sticky, mechanically weaker and excessively swelling film. Still, all the films were relatively mechanically strong, the film resembling a rubber membrane in its elasticity. The results also show that evaporation of the polymer solution was achieved at 20° C. room temperature or skin temperature approximately within five minutes. Example 4 shows that less than half this time is needed to dry the polymeric solution on the skin of a living species.

TABLE 1

| Film Drying Time (Minutes) | Film 1 (D-4) | Film 2 (D-4 with Glycerol) | Film 3 (D3 & D4) |
|---|---|---|---|
| Adhesiveness Score (1–5) | | | |
| 1 | 3 | 2 | 3 |
| 3 | 3 | 2 | 3.5 |
| 7 | 4 | 2 | 4 |
| 10 | 4 | 2 | 4 |
| 15 | 4 | 2 | 4 |
| Stickiness of Layers Together: Score (1–5) | | | |
| 1 | 1 | 2 | 1 |
| 3 | 3 | 4 | 2 |
| 7 | 4 | 4 | 3 |
| 10 | 4 | 0 | 0 |
| 15 | 0 | 0 | 0 |
| Tensile Strength (grams to break 1 cm wide strip) | | | |
| 7 | 30 | 15 | 45 |
| 10 | 30 | 58 | 115 |
| 15 | 58 | 58 | 115 |
| Swelling (grams H$_2$O absorbed per square inch) | | | |
| 1 | 0.555 | 0.35 | 0.060 |
| 3 | 0.125 | 0.90 | 0.120 |
| 7 | 0.130 | 0.90 | 0.125 |
| 10 | 1.140 | 0.90 | 0.130 |
| 15 | 1.150 | 0.90 | 0.132 |

Example 2 shows that a thin hydrogel polymer film based on polyacrylonitrile formed on a surface significantly prevents the absorption of lipophilic substances, such as parathion, into the skin. Parathion, dimethyl-p-nitrophenyl monothiophosphate, is a pale yellow liquid that is practically insoluble in water. It is used as a common agricultural insecticide in a spray, diluted in oils. It is highly toxic if inhaled or absorbed by skin exposure. The following experiment was designed to test the protective effect of a film of hydrophilic hydrogel based on polyacrylonitrile against Parathion.

Skin from the inside of rabbit ears was peeled off and tightly stretched over the mouth of a 50 ml plastic tube over a 23 millimeters diameter circular area. The tube was filled from the bottom with an extracting fluid, mineral oil, to contact the lower part of the skin (dermis). The top of the skin was covered with 0.2 milliliters of 15 weight percent of polyacrylonitrile dissolved in 85 weight percent of dimethylsulfoxide and 15 weight percent of water. This solution was evenly spread over the 23 millimeter diameter skin dish, and left to evaporate to form a continuous layer of the hydrogel film. The thickness of such a film was 183 microns.

The control skin was left intact (without treatment). Three microliters of Parathion $S^{32}$ was placed in the middle of the 23 millimeter diameter skin area and spread over the entire surface. At various time intervals the transport of the radio-labelled Parathion across the skin, either covered by the hydrogel or without the treatment, into the oil phase in contact with the other dermal side of the skin, was tested by collecting an aliquot of the oil phase for measuring the radioactivity of parathion. The results are shown in Table 2. The data indicate that during two hours of skin exposure to parathion the drug was continuously resorbed by the intact skin.

In the case of the skin being coated with a 183 micron thick film of the above polyacrylonitrile hydrogel, almost complete inhibition of the Parathion resorption was observed.

Thus, it is shown a suitable hydrogel film placed on the skin surface prevents the penetration of lipophilic toxic substances across the skin into the body tissues.

TABLE 2

Effect of a Film of Hydrophilic Polyacrylonitrile hydrogel film 183 microns thick on the Penetration of $S^{32}$ Parathion into the Skin of Rabbit Ear

| Exposure Time (mins.) | Radioactivity of $S^{32}$ Parathion in the Skin (cpm) | | Protection (% of Unprotected Control Skin) |
|---|---|---|---|
| | Unprotected (counts per minute) | Hydrogel Protected (counts per minute) | |
| 10 | 1,120 | 56 | 99.5 |
| 20 | 1,320 | 66 | 99.5 |
| 60 | 1,640 | 147 | 99.1 |
| 120 | 1,950 | 351 | 98.2 |

Example 3 describes an application of hydrogel skin coatings for the reduction of personnel contamination in the semiconductor, disc drive, and optical industries.

In the following experiment a 15 weight percent polyurethane hydrogel D-4 was dissolved in 70% medical grade purity of ethanol and 30% deionized distilled water. A thin layer of this hydrogel solution was spread over the skin. The solvent evaporated within three minutes to form a thin, pliable film that contained residual water. This residual water allowed perspiration to pass (by allowing the film to absorb the perspiration, which then passes through the film and then evaporates from the other side), thereby reducing the discomfort associated with the accumulation of moisture inside a barrier glove.

For the experimental studies, about 13 milliliters of the hydrogel was gently smeared over the subject's finger tips and allowed to dry. No hand washing was done before application of the hydrogel, as it was desired to simulate the work environment as closely as possible. The drying time of the hydrogel is determined by the ethanol content and usually takes a few minutes. After drying, the hydrogel surface is shiny, which is significantly different from human skin. This makes it easy to detect any areas that have not been properly protected. In principle, a colored dye could be added that would "show" any areas where the coating is thin or has been damaged by abrasion.

For the fingerprint tests, clean 75 millimeter silicon wafers were used. The wafers were first examined with a microscope (400×) and with a Model 100 SURF SCAN machine for measuring amounts of light scattering, manufactured by Tencor, of California, to detect any preexisting contamination. For the first test the subject was asked to press an uncoated finger against the wafer. A definite fingerprint was observed (Table 3). The test was then repeated with a fingertip that had been coated with the hydrogel. In some cases the contamination was minimal, in several tests no change in the surface could be observed with a Model 100 Surf Scan unit. The hydrogel provided almost complete protection against surface contamination by human hands.

The results presented above are not intended to suggest that employees should handle wafers with their fingers though this might be quite practical in other industries (e.g., ball bearing manufacturing) where tweezers are difficult to use. The major application of the hydrogel material, at least in the semiconductor industry, would be to prevent contamination of the product from skin scales when the employee is using some sort of gripping system (e.g., tweezers) without the usual latex gloves.

To demonstrate the effect of the hydrogel in this area we used a skin scales collecting device. The unit was set up in a class 100 area and a Climet Model 6300 particle counter with a flow rate of 1 CFM was used for the measurement. The subject rubbed his fingers together to generate skin scales without hydrogel protection. The count in this case was quite high, as shown in Table 3. The test was repeated with a coating of hydrogel and the count fell dramatically.

As one skilled in the art can readily see from the results in Table 3, these experiments show that the use of hydrogel coatings does essentially "eliminate" fingerprints and greatly reduces skin scaling.

TABLE 3

Effect of Coating the Fingers with a Hydrogel Film on Contamination of Silicon Wafer

| Group | Fingerprint Test Particles 0.2/sq. in | Skin Scales Shedding Test Particles (0.2–12 microns/cu. ft.) |
|---|---|---|
| Background contamination | 5 | 15–18 |
| Effect of unprotected fingers | 11,200 | 12,000–15,000 |
| Effect of hydrogel coated fingers | 98 | 17–21 |

Particles quantitated by laser scattering system Model 100 SURF SCAN (Tencor, Calif.) and the size was determined by a polarized at 400× magnification.

EXAMPLE 4

In this example, the rate of drying of a solution of a hydrogel polymer applied onto the skin to form an adherent film with adequate mechanical properties was tested, using spontaneous drying under the temperature of the skin surface or using additional hot air generated by a hair dryer. A solution containing 5 grams of polyurethane D-4 in 100 milliliters of a mixture of 70 milliliters of medical ethanol and 30 milliliters of distilled water was applied over the forearm and the skin surface of the hand in a form of an aerosol spray generated by a stainless steel 6 ounce cylinder, pressurized with 200 psi air. Approximately 10 milliliters of the above solution was uniformly sprayed onto the skin. The time was recorded when the stickiness of the wet polymer disappeared and a thin film was formed over the skin surface horny layer, called stratum corneum. It was found that if only the temperature of the skin surface contributes to the evaporation of the solvent, it takes 3.2±1.2 minutes to obtain a dry, non-sticky film onto the skin surface.

A similar experiment was done using a stream of hot air generated by a hair dryer, placed 35 centimeters distant from the sprayed forearm and hand. The heating filament of the dryer was set to 400 watts. We found that under these conditions, the dry film formed after 0.57±0.12 minutes. Thus, using an external source of heat the formation of the final dry film takes less than one minute.

EXAMPLE 5

This example shows the minimum effective concentration of hydrogel needed to cover the hand and significantly reduce contamination of a silicon wafer.

Hydrogel based on polyurethane D-4 was prepared in 70 volume percent ethanol to contain 1, 2, 3, 7 or 10 weight percent of the polymer. The wafer contamination was determined with the SURF SCAN instrument. The following three indicators of the effectiveness were measured:

1. Area of the wafer occupied by contaminating particles;

2. Average haze, which indicates the overall density of spots (sebum) left as a fingerprint on the wafer to scatter light;

3. Stickiness of two surfaces coated with hydrogel was evaluated on a scale 1 to 4: 1 no stickiness, 2 minimal, 3 moderate, 4 strong, generally as described earlier with reference to Example 1.

The procedure for collecting data was as follows: First, background contamination measurements were taken by feeding the wafer into a fixed orientation, through the SURF SCAN instrument. Next an unprotected fingerprint was placed in the center of the wafer and fingerprint contamination measurements made gain on the same wafer. A finger then was coated with the 1% hydrogel solution which was allowed to dry for five minutes. A new print with the coated finger then was placed to the right of the unprotected fingerprinted and the additional contamination was measured. The process was repeated with the 3%, 7% and 10% hydrogel solutions, each fingerprint being placed on a separate location on the wafer. Four people were tested in the experiment. People with the most oily skin were the best subjects because the fingerprints they produced on the wafer surface were large and well above instrumental noise.

The results shown in Table 4 indicate that with 3% and higher concentration of hydrogel complete prevention of wafer fingerprint contamination was achieved, but 1% solution was not effective. However, with increasing concentration of hydrogel the stickiness increases. For practical purposes, 3% concentration of D-4 hydrogel in 70% ethanol is probably optimal to prevent contamination of surfaces with skin secretion products.

TABLE

| Type of Treatment[1] | Area of Contaminating Particles On Wafer Surfaces | Average Haze (Finger-print Density on Wafer Surface) | Stickness Score[3] of Hydrogel Coated Index Finger and Thumb |
|---|---|---|---|
| Background | 0 | 14 | 1.0 |
| Unprotected Finger | 545 | 144 | 1.0 |
| Coating with Hydrogel[2] | | | |
| 1% solution | 344 | 88 | 1.1 |
| 3% | 0 | 0 | 1.3 |
| 7% | 0 | 0 | 1.7 |
| 10% | 0 | 0 | 2.1 |

[1]Data based on testing of four persons, average values are shown.
[2]Same volume of solution of hydrogel was applied to the finger tip (0.3 ml) and let dry for 5 minutes in teh air at room temperature.
[3]Score 1 to 4 was used, 1 no stickiness, 4 very sticky.

EXAMPLE 6

The following example demonstrates that addition of inert fillers into the solution of the hydrogel polyurethane D-4 reduces the stickiness of a dry film thereof coating the skin surface.

While Example 5 shows that hydrogels based on polyurethane D-4 solution at concentration 3% and higher are effective to prevent any measurable wafer contamination, the formed film showed increasing stickiness with increasing concentrations of the hydrogel. This stickiness can be reduced by adding certain powders of insoluble compounds with particle size not exceeding 100 angstroms. Among these compounds it was found that the most effective are thixotropic gel power (CAB-O-SIL) or amorphous silica, manufactured for example by Sigma Chemical Co. or aerosil Degussa (from Merck Co.) or titanium dioxide, and that hydrogels based on polyurethane D-4 have significantly reduced stickiness when mixed with certain doses of such fillers. Aerosil Degussa consists of amorphous silica with particle sizes of 5–10 angstroms.

The method of evaluation the effect of fillers on the contamination of wafers and the stickiness magnitude was the same as in Example 5. Five percent concentration of the hydrogel polyurethane D-4 in 70% ethanol was prepared. Thixotropic gel and aerosil were mixed into the solution to form 0.5, 1.0 and 1.5 percent suspensions. Due to small particle size (5–10 angstroms) of these powders, the suspension was stable, even after sedimenting for 6 hours. After 12 hours the powder suspension sedimented and had to be mixed before use.

The same volume of the same formulation was placed over the finger tip, spread evenly and let dry for 5 minutes in the air at room temperature. For measuring stickiness, the index finger and thumb were coated. Once dry, the coated fingers were pressed together for 30 seconds under pressure of 20–40 grams. After releasing of the pressure, the stickiness of the two coated surfaces was scored on a scale of 1 to 4 in the manner indicated in Example 5.

The results are shown in Table 5. Again, complete prevention of wafer contamination was achieved by coating the finger with 5% D-4 hydrogel film plain or with three different concentrations of fillers. Although the stickiness of either hydrogel was less than minimal (Score 2), the presence of filers based on thixotropic gel or amorphous silica powder reduced the stickiness, the highest concentrations used, especially with thixotropic gel, being found optimal. No stickiness was found and it was found that the smooth coated wafer surface did not cause friction resistance, especially with 1.5% concentration of thixotropic gel in 5% hydrogel D-4 solution of 70% ethanol. The powder was firmly embedded in the hydrogel film formed on the skin surface.

TABLE 5

The effect of mixing of the hydrogel solution with insoluble fine powder on the protection of contamination of wafers with skin secretions and on the stickiness of the hydrogel films.

| Type of Treatment | Average Haze (Figerprint Density on Wafer Surface) | Stickiness Score of Hydrogel/Filler Coated Index Finger and Thumb |
|---|---|---|
| Background Unprotected fingerprint | 17 | 1.0 |
|  | 66 | 1.0 |
| Hydrogel coated: |  |  |
| 5% plain | 0 | 1.5 |
| 5% +Tx 1.5% | 0 | 1.2 |
| 1.0% |  | 1.1 |
| 1.5% |  | 1.0 |
| 5% + AD 0.5 | 0 | 1.4 |
| 1.0 |  | 1.2 |
| 1.5 |  | 1.1–1.2 |

Hydrogel D-4 was used.
Tx refers to thixotropic gel powder.
AD refers to aerosil Degussa amorphous slice particles.

The hydrogels suitable as a liquid glove or second skin coating based on polyurethane should have larger portion of low molecular weight glycol units, around few hundred Daltons in size, which serve as hard blocks in the final film. These blocks are responsible for the mechanical strength of the film, while soft blocks of larger molecular weight glycol units (in thousands of Daltons) contribute to water binding capacity of the final product.

The hydrophilic hydrogels used in the above examples include polyurethane and acrylonitriles. Similar results would be expected using the other above-mentioned hydrophilic hydrogels because they have similar physical properties of hydrophility, flexibility, tensile strength, and resistance to abrasion.

Where described to ensure that workers apply the ordinarily transparent hydrogel film to their hands and faces, a suitable coloring agent or fluorescent agent can be added to the polymeric solution to tint the resulting layer. The hydrogel layer also can serve as a sun screen or as a base on which to apply cosmetic make-up products. Other agents can be added to the polymeric solution to detoxify toxic environmental substances, such as activated charcoal, sulfonate repelling insects, or virici-dal substances such as monoxynol-9 and benzalkonium chloride.

While the invention has been described with reference to a particular embodiment thereof, those skilled in the art will be able to make various modifications to the described embodiment of the invention without departing from the true spirit and scope thereof. It is intended that all elements and steps which perform substantially the same function in substantially the same manner to achieve the same result are within the scope of the invention.

We claim:

1. A method of forming a protecting film on a person's skin, the method comprising the steps of:
   (a) dissolving a hydrophilic hydrogel polymer from the group consisting of hydrophilic polyurethane, polymers and copolymers of acrylonitrile, and polyvinyl acetate with a solvent from the group consisting of ethanol/water, ethyl alcohol, isopropyl alcohol, dimethylsulfoxide, and glycerol to form a polymeric solution;
   (b) uniformly spreading a thin layer of the polymeric solution onto substantially all of a portion of the person's skin;
   (c) drying the layer to form a pliable, tough, hydrogel film which is adhesive to the person's skin;
   (d) absorbing water from perspiration by the person's skin under the layer through an inner surface of the film into the film while blocking passage of greasy seabum from the person's skin;
   (e) passing the absorbed water through the film from the inner surface of the film to an outer surface of the film; and
   (f) evaporating the water from the outer surface of the film.

2. The method of claim 1 wherein step (b) includes uniformly spreading a thin layer of the polymeric solution onto substantially all of the skin of the fingers of a hand of the person.

3. The method of claim 1 wherein step (b) includes uniformly spreading a thin layer of the polymeric solution onto substantially all of the skin of the person's face.

4. The method claim 1 wherein step (a) includes dissolving the hydrophilic hydrogel polymer into the solvent in an amount effective to cause the film to retain 40–65 weight percent water when fully hydrated.

5. The method of claim 1 including mixing a filler powder in the polymeric solution to reduce the stickiness of the protective film.

6. The method of claim 1 including mixing filler powder of inert powder of particle sizes of about 5–10 Angstroms in the polymeric solution in order to reduce the stickiness of the protective film.

7. The method of claim 1 including removing the film by peeling it off the person's skin.

8. The method of claim 6 including removing the film by applying heated water to the film before peeling it.

9. The method of claim 1 including mixing a coloring agent into the polymeric solution to color the hydrophilic hydrogel film.

10. The method of claim 1 including combining an insect repellent with the polymeric solution.

* * * * *